United States Patent [19]

Gahn et al.

[11] Patent Number: 5,162,044
[45] Date of Patent: Nov. 10, 1992

[54] PHACOEMULSIFICATION TRANSDUCER WITH ROTATABLE HANDLE

[75] Inventors: Gerald S. Gahn, Manchester; William J. Buttermore, Chesterfield, both of Mo.

[73] Assignee: Storz Instrument Company, St. Louis, Mo.

[21] Appl. No.: 624,592

[22] Filed: Dec. 10, 1990

[51] Int. Cl.⁵ .............................................. A61B 17/20
[52] U.S. Cl. ................... 604/22; 128/24 AA; 406/169
[58] Field of Search ..................... 604/22; 128/24 AA; 606/169-171

[56] References Cited

U.S. PATENT DOCUMENTS

| | | |
|---|---|---|
| 3,815,604 | 6/1974 | O'Malley et al. . |
| 4,203,444 | 5/1980 | Bonnell et al. . |
| 4,210,146 | 7/1980 | Banko . |
| 4,223,676 | 9/1980 | Wuchinich et al. . |
| 4,577,629 | 3/1986 | Martinez . |
| 4,643,420 | 1/1987 | Spinosa et al. . |
| 4,696,298 | 9/1987 | Higgins et al. . |
| 4,747,820 | 5/1988 | Hornlein et al. ..................... 604/22 |
| 4,753,234 | 6/1988 | Martinez . |
| 4,846,790 | 7/1989 | Hornlein et al. . |
| 4,909,249 | 3/1990 | Akkas et al. . |
| 4,940,468 | 7/1990 | Petillo . |
| 4,988,334 | 1/1991 | Hornlein et al. ..................... 604/22 |
| 5,047,008 | 9/1991 | de Juan, Jr. et al. . |
| 5,055,100 | 10/1991 | Olsen ..................................... 604/22 |
| 5,062,827 | 11/1991 | Wiksell ................................. 604/22 |

Primary Examiner—Stephen C. Pellegrino
Assistant Examiner—Michael Rafa
Attorney, Agent, or Firm—Brooks & Kushman

[57] ABSTRACT

A phacoemulsification transducer or probe utilizing ultrasonic frequencies to treat cataracts, including a rotatable handle to facilitate repositioning of the needle in the eye during surgery while maintaining a comfortable and secure grip on the instrument. The rotatable handle is comprised of a sleeve portion, irrigation tube and connector member. The sleeve portion is secured to the front of the main body of the probe and the connector member is attached to the distal end thereof.

13 Claims, 2 Drawing Sheets

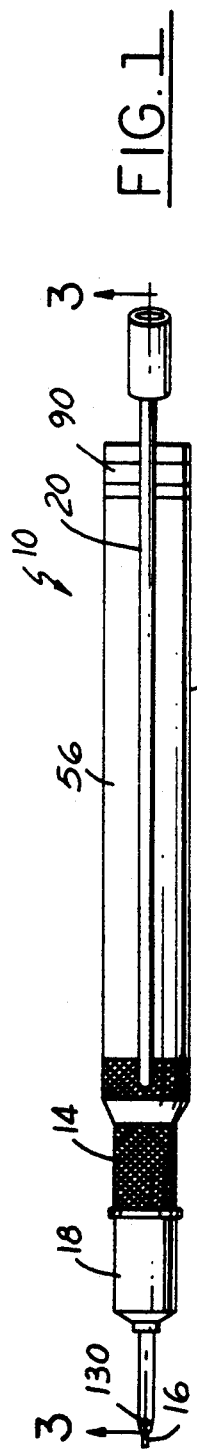
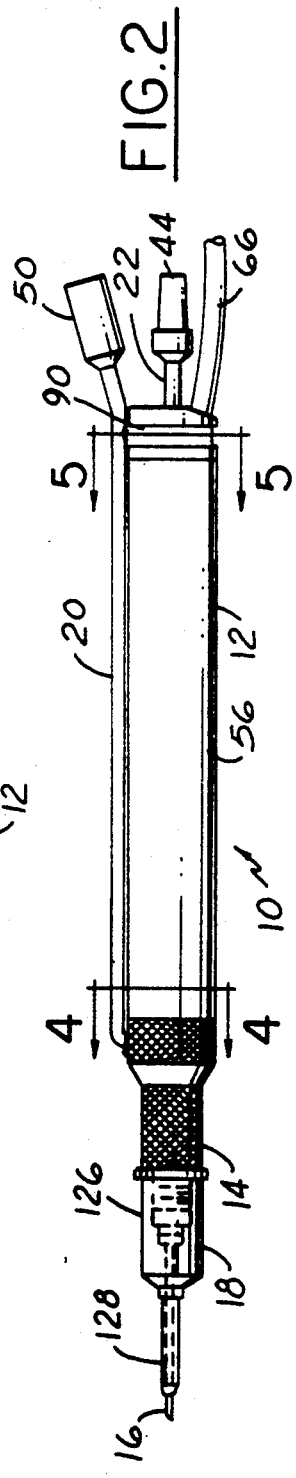
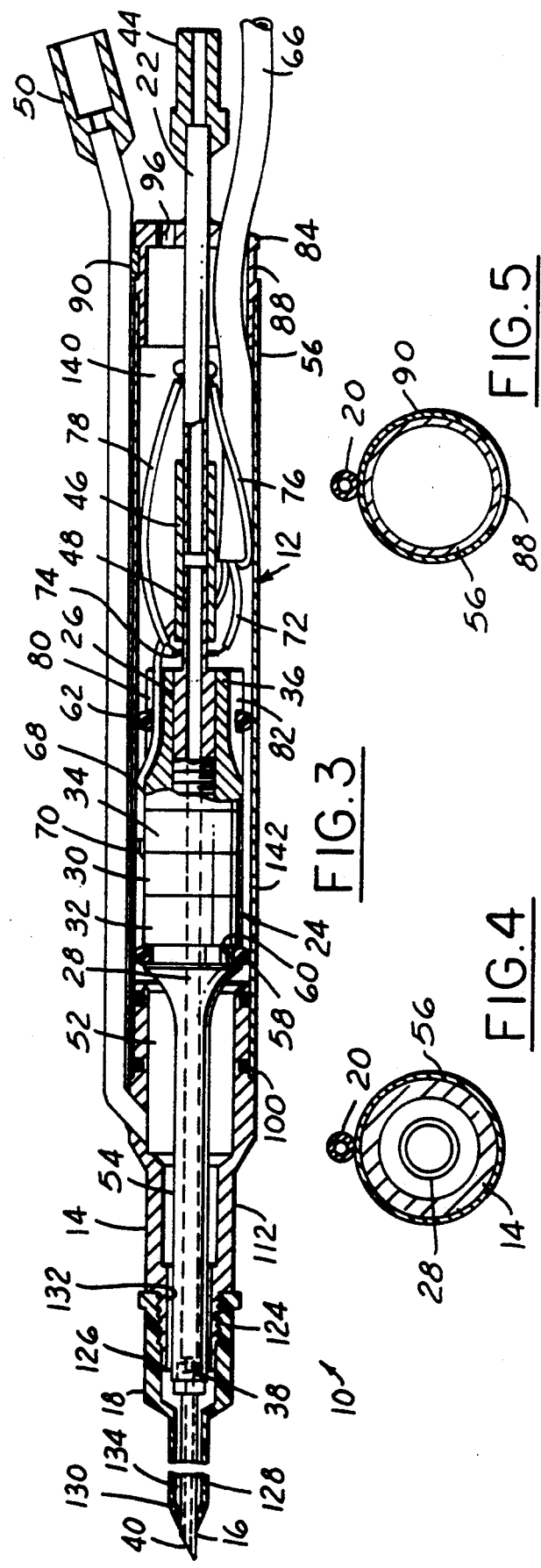
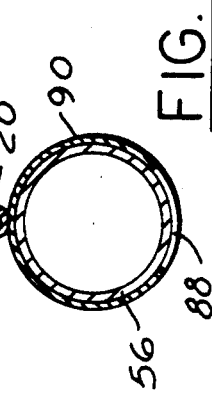

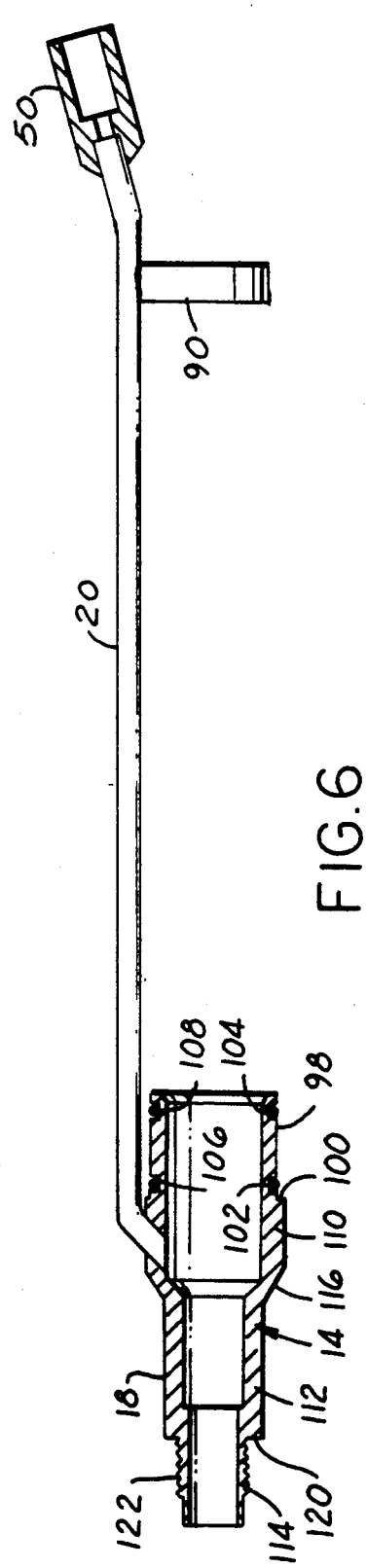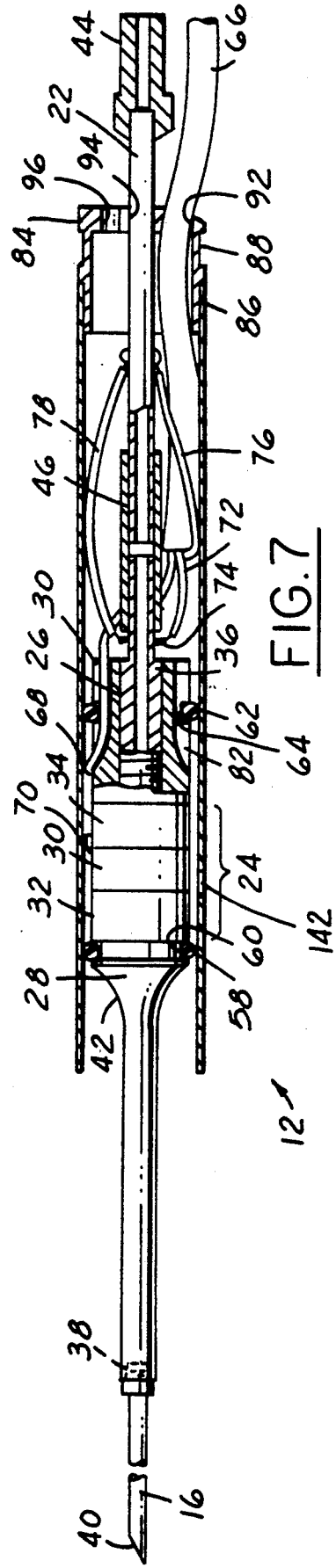

PHACOEMULSIFICATION TRANSDUCER WITH ROTATABLE HANDLE

TECHNICAL FIELD

The invention relates to a surgical instrument which utilizes ultrasonic frequencies to treat cataracts. More specifically, the invention relates to an ultrasonic surgical instrument with a rotatable handle that facilitates ease of positioning and use by the surgeon.

BACKGROUND OF INVENTION

Phacoemulsification refers to the process of ultrasonic disintegration of the lens of a human or animal eye using a vibrating probe which operates at a frequency above the audio range. It is a known surgical procedure for removing cataracts. The probe includes a needle which vibrates at ultrasonic frequencies to shatter the cataract. The shattered debris is withdrawn through an aspiration removal tube.

The needle is mounted on the surgical instrument which sometimes is referred to as a Phacoemulsification handpiece or "phaco probe". A number of such handpieces or probes are known, the most common of which utilizes piezo-electric transducers to produce the vibrations of the needle at ultrasonic frequencies. Commonly-owned application Ser. No. 07/251,531, filed on Sep. 30, 1988 describes and claims one such phacoemulsification probe that is commercially available from the assignee of the present invention, Storz Instrument Company of St. Louis, Mo.

Phaco probes typically require a means for aspiration and/or irrigation of the operation site. A problem with such devices, however, is that the structure for aspirating and/or irrigating the site is typically rigidly fixed to the surgical instrument. As the instrument is rotated during the operation, the structure rotates and interferes with the surgeon's hand. The surgeon's grip on the instrument, and likewise his control over it, thus can be compromised.

A representative device is shown in U.S. Pat. No. 4,634,420, to Spinosa et al., which discloses an apparatus and method for the surgical removal of tissue such as a cataract using a needle vibrated at ultrasonic frequencies. The tubing on this device will conflict with the surgeon's grip on the tool as it is maneuvered during the operation, thereby increasing the difficulty of the surgical procedure and decreasing the comfort and grip on the instrument by the surgeon.

U.S. Pat. No. 4,846,790, to Hornlien et al., discloses an ultrasonic surgical system with an aspirator/irrigation manifold. The aspiration tube is placed along the outside of the surgical instrument and, as the instrument is rotated, the tube will conflict with the surgeon's hand and fingers, thereby possibly encumbering the surgeon during the surgical procedure.

DISCLOSURE OF INVENTION

The present invention provides a phacoemulsification transducer or probe of the type previously disclosed in application Ser. No. 07/251,531 including the additional improvement of a rotatable handle. The rotatable handle generally is comprised of a sleeve or grip portion having an irrigation tube and a connector member which fit on the body of the probe.

The hollow body of the sleeve or grip portion is positioned over a cone-shaped front end of the main body. Once properly seated onto the main body, the connector member is clipped or snapped into a groove provided near the distal end of the main body. To complete the assembly, the needle and irrigation cap are threadedly secured to the main body and sleeve portion, respectively.

In operation, the probe is held between the thumb and forefinger in a fashion commonly used with writing implement and other instruments of similar size. The probe is oriented such that the irrigation tube runs along the top portion of the main body to ensure a comfortable finger grip throughout the surgical procedure. As necessity dictates, the operator may re-locate the hollow blade on the eye while maintaining the same overall orientation of the probe by merely rotating the main body relative the grip portion.

The slender shape of the device and the ability to easily maintain the proper orientation of the probe through the rotation capabilities of the main body relative to the grip portion results in improved comfort for the operator and improved surgical techniques.

The ability to maintain a comfortable hand position while re-locating the hollow blade improves the surgical technique and enhances the surgical procedure.

Accordingly, it is a general object of the invention to provide an improved phacoemulsification probe which can easily adjust the orientation of the tip thereof while maintaining a comfortable hand and finger grip.

It is also an object of the present invention to provide a phacoemulsification probe with a grip position which is rotatable relative to the main body of the probe to facilitate handling of the device.

It is another object of the invention to provide a phacoemulsification probe for the surgical treatment of cataracts, the probe having a main body with a needle instrument for breaking up and removing the cataractous lens in the eye. The probe includes a drive means for vibrating the needle and a vacuum means for removing the material and debris caused by the operation procedure. The phacoemulsification probe is provided with a means for supplying power to the drive means. The device also has a main body having an outer surface portion and a retention portion. A grip or sleeve portion which is knurled to improve the grasp of the surgeon contains an irrigation tube and a connector member.

The grip portion overlays and is in sealed relation with the outer surface portion of the main body and spaced therefrom to form a chamber which is in fluid flow communication with the irrigation tube. The retainer is snap-fitted to the retention portion of the main body while the grip portion is positioned over the forward portion of the main body. The grip portion is rotatable relative to the main body so that the operator may position the irrigation tube out of the way during the operation procedure, in order to maintain a comfortable grasp of the instrument while enabling repositioning of the needle at the desired location and orientation.

A cap is affixed to the grip portion improving proper irrigation of the eye during the operation. A series of o-rings allow frictional movement of the grip portion relative to the main body and enhance the watertight integrity of the instrument.

The invention, together with additional features and advantages thereof, may best be understood by reference to the following description taken in connection with the accompanying illustrations.

BRIEF DESCRIPTION OF THE FIGURES

FIGS. 1 and 2 are top and side elevational views, respectively, of the present invention;

FIG. 3 is a side cross-sectional view of the invention, taken along line 3—3 in FIG. 1;

FIGS. 4 and 5 are cross-sectional views of the present invention taken along lines 4—4 and 5—5, respectively, of FIG. 2;

FIG. 6 illustrates the rotatable grip, tube and connector portion of the invention; and FIG. 7 illustrates the main body portion of the invention.

BEST MODE FOR CARRYING OUT THE INVENTION

The inventive phacoemulsification instrument 10 is shown in FIGS. 1-7. The phaco probe generally comprises a main body 12, a sleeve or grip portion 14, a needle 16, an irrigation cap 18, an irrigation tube 20 and an aspiration tube 22.

The main body 12, which particularly is shown in FIGS. 3 and 7, includes a piezoelectric transducer 24. As specified more particularly in application Ser. No. 251,531, the ultrasonic transducer 24 is located between a reflector 26 and a resonator 28. The transducer comprises an electrode 30, preferably constructed of unhardened No. 01 carbon steel or beryllium copper situated between two piezoelectric crystals 32 and 34. The crystals are constructed of a modified lead zirconate titanate ceramic material, formed into rings, silver coated for electrical conductivity. Preferred crystals are marketed under the trade name PXE by the Electronic Components and Materials Division of North American Phillips Corporation.

The reflector 26 is fastened to the resonator 28 by a hollow threaded tube 36 which mates with corresponding threaded portions in the reflector and resonator. The hollow tube 36 and resonator 28 are preferably constructed of 6AL-4V titanium. The reflector 26 is constructed of No. 17 tungsten.

The components of the transducer assembly are threaded and pressed together. The transducer 24 (comprising hollow ringed elements 30, 32 and 34) is positioned on the tube 36 and the resonator and reflector are threaded onto the ends. The transducer is compressed between the resonator and reflector in the manner stated in application Ser. No. 251,531; it is not necessary to discuss it further in this application since it is not part of the present invention.

Electric excitation of the crystals 32 and 34 by the electrode 30 causes the needle 16 to oscillate as is known in the art. The vibrating needle can be used to fracture hard materials such as cataracts in the human eye.

The needle 16 is attached as by threads 38 to the forward end of the resonator 28. Any needle known in the art, such as Model No. IA-145 available from Storz Instrument Co., is screwed into the threaded end of the resonator. The needle preferably has a slanted or angled tip 40 and vibrates in a longitudinal mode when the transducer is activated. The vibrational displacements typically are about 0.001 to 0.005 inches, depending upon the strength and frequency of the electrical drive signal applied to the transducer. The vibration of the needle normally occurs at the oscillation frequency of the piezoelectric crystals 32 and 34. Curved region 42 of the resonator 28 acts as a horn in order to impedance-match the crystals with the needle. The resonator 26, as a whole, functions as a one-quarter wave length transmission line (at the crystal frequencies) on which the needle acts as a load.

As the cataract is being shattered and broken up by the vibrating needle 16, the debris is withdrawn through the aspiration tube 22 under the influence of a vacuum. The vacuum is generated by a vacuum source (not shown) that is attached to a male leur connector 44 by conventional plastic tubing or the like. As shown in FIGS. 3 and 7, the needle 16 is hollow and the aspiration channel extends through the resonator 28, the hollow tube 36 and the aspiration tube 22. A flexible connector tube 46 is used to connect aspiration tube 22 to a flange 48 on the hollow tube 36 in order to maintain continuity of the aspiration channel throughout the probe.

As the cataract debris is being withdrawn from the eye, some of the fluid within the eye is withdrawn with it. To replace that fluid, saline, basic salt solution or any other conventional surgical replacement fluid is inserted into the eye through irrigation tube 20. A female leur connector 50 attaches the irrigation tube 20 to a source of irrigation fluid (not shown), preferably by use of flexible conventional plastic tubing or the like.

Fluid which flows through the irrigation tube 20 passes through chambers 52 and 54 and enters the surgical site through one or more small openings 130 in the forward end of the irrigation cap 18 (as described in more detail below).

A metal sleeve 56 or "handle portion" is positioned on the outer surface of the main body 12. O-ring 58 positioned in annular groove 60 on the resonator 28 and O-ring 62 positioned in annular groove 64 on the reflector 26 hold the sleeve 56 in place. O-ring 58 acts to seal the transducer 24 from irrigation fluid present in chamber 52.

A tri-wire electrical lead 66 is attached to the main body 12. The lead electrifies the electrode 30 of the transducer and, when electrified, activates to excite the transducer and vibrate the needle 16. One of the wires 68 in the lead 66 is connected to the electrode 30 (as by solder connection 70) and supplies power to it. Another of the wires 72 is connected to ring 74 (grounding lug) situated on the tue 36. The third wire 76 is a ground wire connected to the aspiration tube 22. In addition, a redundant grounding wire 78 is provided in the main body and connects the ring 74 to the tube 22.

A pair of opposed slots 80 and 82 are situated on the outer surface of the reflector 26. One of the slots 80 is used to hold the wire 68 so it can pass under the O-ring 62. The other slot 82 is used to allow the potting matrix or medium to pass under and around the O-ring 62, as discussed below.

An end cap 84 is positioned at the distal end of the main body 12. The cap has an annular flange 86 for mating with the sleeve 56, i.e. the sleeve 56 fits over the flange 86 to form a unitary main body 12. The end cap 84 also has an annular groove 88 which mates with and holds in place the ring-like connector member 90 discussed below.

The end cap has three openings 92, 94 and 96 in its rear face. Opening 92 is used to allow electrical lead 66 to be positioned in and extend therethrough. Aspiration tube 22 is situated in opening 94. Opening 96 is an air escape port which is eventually filled with the potting material after the probe is assembled (as discussed below).

The rotatable handle mechanism includes the sleeve or grip portion 14, the irrigation tube 20 and the connector member 90. The grip portion 14 is connected in any conventional manner to the irrigation tube 20, such as by soldering, welding or the like. As shown in FIGS. 3 and 6, the tube 20 is positioned to be in open communication with the interior of the hollow grip portion 14 in order for irrigation fluid to pass therethrough.

The exterior surface of the grip portion 14 has a reduced step-like annular portion 98 defined by shoulder 100. When the grip portion is assembled on to the main body 12, the sleeve 56 slides over the portion 98 and abuts against the shoulder 100 (as shown in FIG. 3). A pair of O-rings 102 and 104 situated in annular grooves 106 and 108 on the grip portion act as seals and prevent fluids from leaking from the chamber 52. The O-rings also help frictionally hold the sleeve in place on the grip portion and yet allow rotation of the sleeve 56 relative to the grip portion 14 when desired.

As shown in FIGS. 3 and 6, the grip portion 14 has three different diameter portions, 110, 112 and 114 separated by an annular angled section 116 and a shoulder 120. Threads 122 are provided on portion 114 of the grip portion 14 and are adapted to mate with internal threads 124 on the irrigation cap 18. The external surface of the grip portion 14 is preferably knurled or textured (as shown in FIG. 1) for ease of grasping by the surgeon.

The cap 18 is preferably made of a soft, flexible plastic material in order to seal and secure the cap to the grip portion. The cap 18 has a larger diameter sleeve portion 126 which is attached to the grip portion and a smaller diameter sleeve portion 128 which fits over the needle 16. The end of the sleeve portion 128 has one or more small openings or holes 130 in order to allow irrigation fluid to flow into the operation site. Irrigation fluid which enters the irrigation tube 20 at connector 50, flows into cavity 52, into cavity 54, along the annular space 132 between the resonator 28 and the inside of portion 114, along the annular space 134 between the sleeve portion 128 and the needle 16, and exits through holes 130.

The connector 90 is a band or ring-like structure which is attached as by welding or soldering to the irrigation tube 20. The connector 90 is positioned on the tube 20 such that the connector 90 will mate with groove 88 on the end cap 84 when the phaco probe instrument is assembled.

In order to assemble the invention, the main body 12 is first constructed. The transducer 24 is assembled to the resonator and reflector, and the O-rings 58 and 62 positioned in place. The end cap 84 with lead wire 66 and aspiration tube 22 positioned on it is then attached by connection sleeve 46 to the flange 48. The internal wires of the lead 66 are soldered or otherwise secured in place. The sleeve 56 is positioned over this subassembly forming the main body 12.

The inner chamber 140 which exists inside the sleeve 56 is then filled with a silicone or another conventional "potting-type" material. The material is introduced into the chamber 140 through opening 142 in sleeve 56. As the material fills the space around the transducer 24 and reflector 26, it passes through slot 82 (in order to bypass O-ring 62) and also fills the chamber which houses wires 72, 76, 78, etc. Opening or port 96 in end cap 84 allows the air in chamber 140 to escape when the potting material is forced into it through opening 142. The chamber 140 is completely filled when the potting material starts to exit from port 96.

The main body 12 is then assembled to the rotatable handle mechanism. The resonator 28 is positioned inside the hollow grip portion 14; the grip portion 14 is positioned over the front of the main body 12 until the sleeve 56 is firmly seated on step-like annular portion 98 and the resonator protrudes through the front of the grip portion. At the rear end of the main body, the clip-like connector member 90 is snapped into the groove 88 where it is free to rotate, but not move longitudinal, relative to the longitudinal axis of the probe.

If the needle 16 has not previously been connected to the resonator 28, it is then screwed into position at this point. (The needle is typically disposable and installed by the surgeon at the time of surgery.) The irrigation cap 18 is then positioned over the needle and threaded onto the grip portion 14 forming the completed phaco probe.

Due to the structure and construction described above, the grip portion/irrigation tube/connector ring assembly rotates relative to the sleeve 56 and main body portion 12. Since the connector ring 90 is loosely snap-fitted in place in the groove 88 and the sleeve 56 is held from rotating by the O-rings 58 and 62, as well as the potting material, the rotation of the grip portion/irrigation tube/connector ring assembly can be carried out easily by hand. The limited friction caused by the small O-rings 102 and 104 prevents the sleeve from rotating too freely.

In use, the surgeon holds the phaco probe in one hand somewhat like a writing implement. The rotatable mechanism is adjusted (rotated relative to the sleeve) in order to position the irrigation tube 20 in the space facing outwardly between the user's thumb and forefinger. In this manner, the irrigation tube 20 will not interfere with the surgeon grip or ability to hold and maneuver the probe. If the surgeon desires to rotate the needle in order to orient or change the slanted end 40 of the needle 16 to another position, this can be accomplished by a simple rotation of the main body relative to the grip portion, thereby keeping the irrigation tube 20 away from contact and interference with the surgeon's hand. As is evident from the above, the present invention provides a phaco probe for shattering cataracts, removing the debris and irrigating the surgical site which is easier to use and more comfortable to hold. The invention also provides a relatively small instrument which is light and easy to use and where the surgeon can maintain precise and accurate control thereof at all times.

All of the external components of the phaco probe, except for the irrigation cap 18 are made of a durable, reusable, autoclavable material, such as No. 304 stainless steel. This includes the grip portion 14, the irrigation tube 20, the sleeve 56, the end cap 84, the aspiration tube 22 and the connector member 90. Since the irrigation cap 18 is silicone, it is disposable and a new cap can be used for each operation.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

What is claimed is:

1. A phacoemulsification probe comprising:

an elongated main body portion having a needle at one end, a transducer positioned therein, and cap means at the other end;

said main body portion also having a resonator positioned therein proximal to said needle;

rotatable grip means having a sleeve means rotatably positioned at said one end of said main body portion and forming a chamber around said resonator, said grip means having a clip means rotatably positioned on said cap means, and having an elongated tube means connecting said sleeve means and said clip means; and irrigation means in fluid flow communication with said chamber in which said resonator is positioned.

2. A phacoemulsification probe for surgical treatment of cataracts comprising:

a main body having a needle means used for shattering said cataracts;

a drive means for vibrating said needle means;

vacuum means for removing material and debris resulting from the operation procedure;

means for supplying power to said driving means;

said main body having an outer sleeve portion and a retention portion;

a grip portion having an irrigation tube and a connector member;

said grip portion overlaying and in sealed relation with said outer sleeve portion of said main body and spaced therefrom to form a chamber in fluid flow communication with said irrigation tube;

said connector member being in snap-fitted relationship to said retention portion when said grip portion is overlaying the outer sleeve portion of said main body whereby to retain the grip portion on said main body; and said grip portion and said connector member being rotatable relative to said main body so that the surgeon may position the irrigation tube out of the way during the operation procedure whereby to maintain a comfortable finger grip while obtaining the desired location of said needle means.

3. The phacoemulsification probe as set forth in claim 2 further comprising a series of O-rings enabling frictional movement of said grip portion relative to said main body, and enhancing the fluid-tight integrity of said main body.

4. The phacoemulsification probe as set forth in claim 2 further comprising cap means attached to said grip portion and surrounding said needle means.

5. The device of claim 4 wherein said main body further comprises a tapered end which cooperates with said grip portion providing a fluid-tight seal to said chamber thereby directing the flow of fluid into said cap.

6. The device of claim 4 wherein said cap has at least one opening located on the end adjacent the needle means to direct a flow of fluid from said chamber onto the eye.

7. The device of claim 4 wherein said cap is attached to said grip portion by co-operable means including threads on said cap and matching threads on said grip portion.

8. The device of claim 4 wherein said cap is hollow to allow said needle means to be axially and rotationally slidable therein.

9. The device of claim 2 wherein said irrigation tube further comprises a connector means for attaching said irrigation tube to a fluid supply means.

10. The device of claim 2 wherein said irrigation tube is upwardly angled at one end to provide clearance of said connector means over said power supply means allowing free rotation of said grip portion relative to said main body.

11. The device of claim 10 wherein said irrigation tube is downwardly angled at the other end to provide a gradual bend at the point of attachment to said grip portion.

12. The device of claim 2 wherein said connector member is generally curved and located on said irrigation tube enabling a snap-fit relationship with said retention portion.

13. The device of claim 2 wherein said connector member is affixed to said irrigation tube.

* * * * *